US005792176A

United States Patent [19]

Chang

[11] Patent Number: 5,792,176

[45] Date of Patent: Aug. 11, 1998

[54] ACUPRESSURE PATCH AND METHOD OF USE

[76] Inventor: Henry H. Chang, Apt. 1313, 1900 Frontage Rd., Cherry Hill, N.J. 08034

[21] Appl. No.: 762,069

[22] Filed: Dec. 9, 1996

[51] Int. Cl.$^6$ .......... A61B 17/00; A61B 19/00

[52] U.S. Cl. .......... 606/204; 606/189; 600/9; 600/15; 128/898

[58] Field of Search .......... 606/204, 189, 606/201; 601/134; 128/907, 898; 600/9, 15; 602/53

[56] References Cited

U.S. PATENT DOCUMENTS

| | | | |
|---|---|---|---|
| 658,027 | 9/1900 | Steiger | 600/15 |
| 4,162,672 | 7/1979 | Yazaki | 600/15 |
| 4,344,421 | 8/1982 | Bareiss | 606/204 |
| 4,391,270 | 7/1983 | Uragami | 600/15 |
| 4,798,194 | 1/1989 | Amishima | 600/15 X |
| 5,084,003 | 1/1992 | Susic | 600/13 |
| 5,405,310 | 4/1995 | Yoo | 606/204 |
| 5,405,357 | 4/1995 | Rowe-Lanzisera et al. | 606/204 |
| 5,531,675 | 7/1996 | Yoo | 606/189 |
| 5,551,173 | 9/1996 | Chambers | 36/44 |
| 5,624,385 | 4/1997 | Hwang | 606/204 |

FOREIGN PATENT DOCUMENTS

| | | | |
|---|---|---|---|
| 0197831 | 10/1986 | European Pat. Off. | 606/189 |
| 2566660 | 1/1986 | France | 606/189 |
| 2574288 | 6/1986 | France | 606/189 |
| 0267909 | 5/1989 | Germany | 606/204 |
| 404269973 | 9/1992 | Japan | 606/204 |
| 404269974 | 9/1992 | Japan | 600/15 |
| 405049706 | 3/1993 | Japan | 600/15 |
| 2176707 | 1/1987 | United Kingdom | 600/15 |
| WO8100357 | 2/1981 | WIPO | 600/15 |

OTHER PUBLICATIONS

McCall "Auricular acu mold pressure therapy and acu mold disc therapy" Product information guide Jul. 19, 1977.

Walter "Acupressure for weight control" FEDRIP, May, 1995.

*Primary Examiner*—V. Millin
*Assistant Examiner*—Kelly O'Hara
*Attorney, Agent, or Firm*—Lennox & Murtha

[57] ABSTRACT

An acupressure patch for providing a controlled pressure to a selected point on the skin of a patient for a selected period of time is disclosed. The patch includes a rigid nub fixedly mounted to a flat rigid pressure plate. The pressure plate is positioned on an adhesive disc and held in place by an adhesive ring. The nub sits in an aperture such that it is not covered with any adhesive. A cushioning pad may also be provided between the pressure plate and the adhesive disc. The acupressure patch provides a low profile apparatus which can be secured to a patient's skin to provide adequate pressure to be effective but not to irritate the skin.

17 Claims, 1 Drawing Sheet

ACUPRESSURE PATCH AND METHOD OF USE

BACKGROUND OF THE INVENTION

This invention is related to the field of acupressure. In particular, the invention is directed to an acupressure patch and a method of applying acupressure.

It has long been the practice for Eastern medical practitioners to employ needles during acupuncture to redirect and improve the flow of energy in the patient's body. The needles must be inserted in the skin of the patient at selected points by highly skilled professionals. The needles may be left in the skin for a period of time as the acupuncturist determines is necessary but they must be removed before the patient leaves the office. Since the needles penetrate the skin, the acupuncturist must guard against the risk of infection to himself and to the patient.

Acupressure is similar to acupuncture but a gentle controlled pressure is applied to the point on the skin, rather than inserting a needle. While the points to which the pressure are applied are the same, since there are no needles inserted into the skin, there is no risk of infection and less treatment anxiety in the patient. The patients can be instructed themselves to place the acupressure patches to certain areas of the skin for the treatment of certain problems.

Various devices have been developed to provide pressure to the skin surface. For example, U.S. Pat. No. 3,987,787 discloses a process and device for alleviation of muscular and non-muscular pain and discomfort. One or more rigid objects are embedded on an adhesive base. The base is pressed against the skin, with the objects facing the skin.

U.S. Pat. No. 4,479,495 discloses an acupressure point stimulator device. A band is wrapped around a body part of the patient. A stimulator is attached to the inside of the band. The stimulator may be shaped to provide a force at a selected direction to the skin surface of the patient.

U.S. Pat. No. 5,470,304 discloses an apparatus and method for providing pressure point therapy. A belt is wrapped around the patient's waist. Threaded pins are driven into apertures in a main panel in the belt, providing pressure to points on the lower back.

Magnetic fields have been used to improve the energy in the human body as well as used to improve healing of specific injuries. Magnets have been applied to shoe inserts and mattress pads to create a feeling of well being and high energy.

SUMMARY OF INVENTION

It is an object of an aspect of the present invention to provide an acupressure patch which will apply pressure at a selected point on the skin of a patient.

It is another object of an aspect of the present invention to provide a magnet that can be selectively attached to the skin of a patient at a selected point.

It is a further object of an aspect of the invention to provide an apparatus for applying pressure to the surface of a patient's skin at a selected point while providing a magnetic field at that same point.

It is a further object of an aspect of the invention to provide a device during the acupressure therapy to enhance the result of the acupressure therapy.

In accord with one aspect of the invention, an apparatus for providing a controlled pressure to a selected point on the skin of a patient for a selected period of time is provided. An adhesive disc has a first surface and a second surface. An adhesive material is applied to the first surface. A substantially flat pressure plate has a first face and a second face. The first face is adhered to the first surface of the adhesive disc. A nub is mounted to the pressure plate at a predetermined position on the second face of the pressure plate. An adhesive ring has a first side, a second side and an aperture. An adhesive material is disposed on the first side. The second side is in contact with the pressure plate and the adhesive disc. The nub is disposed in the aperture.

Certain implementations of this aspect of the invention provide that: the nub is integrally formed with the pressure plate; the nub is a magnetized.

In accord with another aspect of the invention, an acupressure patch for the application of a limited, controlled pressure to a precise point on the skin surface of a patient is provided. An adhesive disc has a first surface and a second surface. The first surface has a disc surface area. An adhesive material is applied to the first surface. A pressure plate has a substantially flat profile, a first face and a second face. The first face is adhered to the first surface. The first face has a plate surface area which is less than the disc surface area such that a flange is defined in the adhesive disc about the periphery of the pressure plate. A nub is mounted to the second face of the plate having a top nub profile area which is less than the plate surface area.

Certain implementations of this aspect of the invention provided that: an adhesive ring has a first side, a second side and an aperture, wherein an adhesive material is applied to the first side of the adhesive ring, the second side of the adhesive ring contacts the second face of the pressure plate, the second side of the adhesive ring contacts the first surface of the adhesive disc, and the nub is disposed in the aperture; a magnet is mounted to the adhesive disc; the nub is a magnet; the pressure plate is a magnet.

In accord with another aspect of the invention, a pressure patch for the application of a limited, controlled pressure to a precise point on the skin surface of a patient for an extended period of time is provided. An adhesive disc has a first surface and a second surface. An adhesive material is applied to the first surface. A pressure plate has a substantially flat profile, a first face and a second face. The first face is adhered to the first surface such that a flange is defined in the adhesive disc about the periphery of the pressure plate. A nub is mounted to the second face of the plate. A magnet is mounted to the adhesive disc at a fixed position.

Certain implementations of this aspect of the invention provide that: the magnet is mounted in a cavity disposed in the nub; the magnet is the nub; the magnet is the pressure plate and the nub; the magnet is a pad mounted to first surface of the adhesive disc under the pressure plate.

In accord with another aspect of the invention, a method is provided for applying acupressure employing an acupressure patch having an adhesive disc, a pressure plate adhered to the adhesive disc, a nub mounted to the pressure plate at a predetermined position and a flange attached to the adhesive disc and disposed about the pressure plate wherein an adhesive material is disposed on the flange. An acupressure point on the skin surface is selected to apply the acupressure. The nub is positioned on the acupressure point. The plate is pressed onto the skin. The flange is pressed onto the skin surrounding the acupressure point such that the adhesive material connects the skin and the flange.

Certain implementations of this aspect of the invention provide that: the acupressure patch further includes a release paper disposed over the adhesive material on the flange and the method further comprises removing the release paper before pressing the flange onto the skin; the acupressure patch includes an adhesive ring having a first side, a second side and an aperture, wherein adhesive is disposed on the first side, the second side is in contact with the pressure plate and the adhesive disc, and the nub is disposed in the aperture.

DESCRIPTION OF PREFERRED EMBODIMENTS

Figure 1:
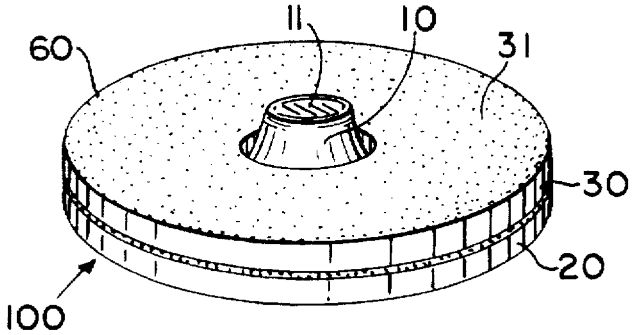
FIG. 1 is a front perspective view of an acupressure patch in accord with an aspect of the invention.
Figure 2:
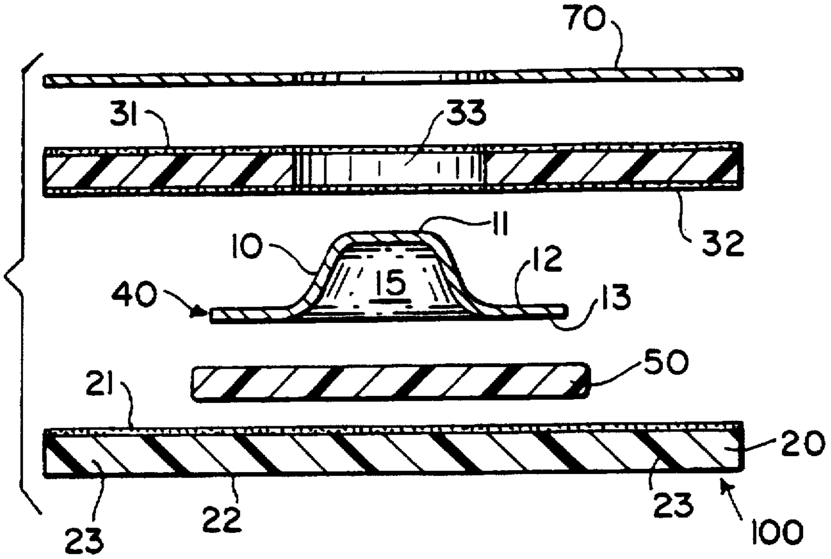
FIG. 2 is a cut-away, exploded view of the acupressure patch of FIG. 1.

Referring to FIGS. 1 and 2, the acupressure patch 100 in accord with an aspect of the present invention includes a raised nub 10 located in the center of an adhesive the first side 31 of an adhesive ring 30, as discussed below. The periphery of the adhesive surface is a flexible flange 60. During use, the head 11 of the nub is positioned on the skin surface to which pressure is desired to be applied. The flange is then pressed against the skin. The flange thus secures the nub against the skin at a controlled pressure.

Figure 4:
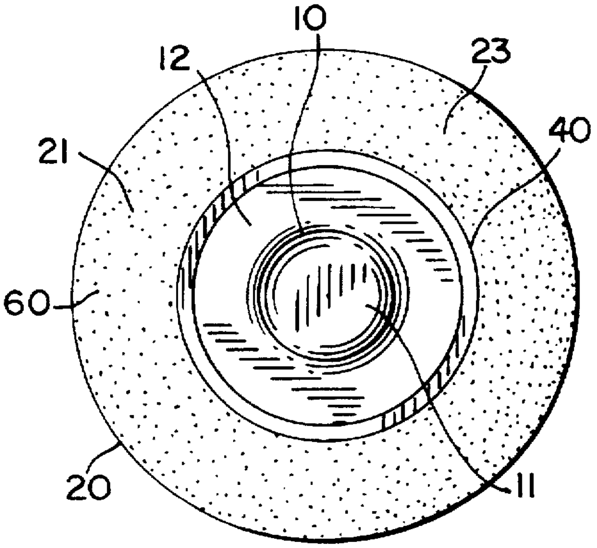
FIG. 4 is a top elevation view of an acupressure patch in accord with an aspect of the invention.
Figure 5:
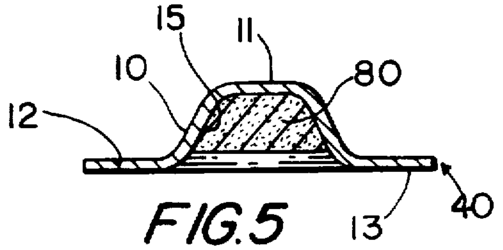
FIG. 5 is a cut-away, side view of the nub and pressure plate of the acupressure patch.

Referring to FIGS. 2 and 4, an adhesive disc 20 has a first surface 21 and a second surface 22. As currently preferred, the disc is thin and flexible and has a circular profile. The adhesive disc may be made of a fabric or a thin plastic sheet. However, other shapes can be employed and still practice the invention. In particular, in certain applications, it may be desirable to shape the adhesive disc to better fit the anatomy of the patient near the pressure point.

Referring specifically to FIG. 2, an adhesive material is applied along the first surface 21. Preferably, the entire first surface is covered with the adhesive material, however, in certain applications, this may not be necessary. The adhesive may be of the type typically used for consumer adhesive bandages. Other adhesives may also be acceptable.

A pad 50 (see FIG. 2) is located on the first surface 21 of the adhesive disc 20. Preferably, the pad is centrally disposed on the adhesive disc and the pressure plate 40 (discussed below) is positioned directly on the pad. The pad will then provide a target and a cushion for the user's finger when applying the acupressure patch.

Figure 3:
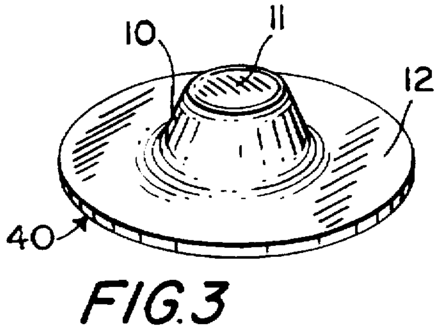
FIG. 3 is a front perspective view of a pressure plate and nub of he acupressure patch of FIG. 1.

Referring to FIGS. 2 and 3, the pressure plate 40 has a substantially flat profile, a circular periphery, a first face 12 and a second face 13. Preferably, the pressure plate is made of metal or some other rigid material. A nub 10 is located at the center of the second face and integrally formed with the pressure plate. The nub 10 is hollow, forming a cavity 15 (see FIG. 2). The nub and the pressure plate may be separately formed and assembled if desirable and the nub may be solid. As shown in the drawings, the nub head 11 is a flat surface with rounded corners. The nub head can also be pointed or rounded, as a particular application requires.

Referring to FIG. 2, a thin, flexible adhesive ring 30 has a first side 31, a second side 32 and a central aperture 33. The aperture is sized to accept the nub 10 (see also FIG. 1). An adhesive material is applied to the first side, preferably covering the first side but this is not necessary. Adhesive material may also be applied to the second side if desirable, but this is not necessary. The adhesive may be of the type typically used for consumer adhesive bandages. Other adhesives may also be acceptable.

Referring again to FIG. 2, to assemble the acupressure patch 100, the pad 50 is positioned at about the center of the first surface 21 of the adhesive disc 20. The adhesive on the first surface maintains the pad in position. The second face 13 of the pressure plate 40 is then positioned centrally on the first surface of the adhesive disc (see FIGS. 2 and 4). The surface area of the adhesive disc is larger than the surface area of the pressure plate so that a peripheral portion 23 of the adhesive disc covered with adhesive material extends beyond the periphery of the pressure plate. The head 11 has a top profile area that is less than the plate surface area (see FIG. 4) such that the pressure plate provides a stable base for the nub. At this stage of assembly, the acupressure patch can be used, employing the peripheral portion as a flange 60 to adhere to the patient's skin. However, it is preferred that the adhesive ring 30 be employed and the surface 31 adheres to the skin to better maintain the nub 10 in position.

The aperture 33 in the adhesive ring 30 is slipped over the nub 10. The second side 32 of the ring is pressed against the first surface 12 of the pressure plate 40 and the first surface 21 of the adhesive disc 20. The surface area of the adhesive ring is larger than the surface area of the second face of the pressure plate so that a peripheral portion of the adhesive ring extends beyond the periphery of the pressure plate. The peripheral portion 23 of the adhesive disc adheres to the peripheral portion of the adhesive ring to form a flange 60 of flexible material about the pressure plate. A release paper 70 is removably positioned on the first side 31 of the adhesive ring.

To apply the acupressure patch 100, the proper pressure point is located by a care giver. This is typically done by the acupressurist and patient himself after instruction. The release paper 70 is removed, exposing the adhesive on the first side 31 of the adhesive ring 30. The nub 10 is positioned directly on the pressure point as the care giver presses his finger on the pad 50. The head 11 of the nub is thus pressed into the skin. The flexible flange 60 is pressed against the skin such that the adhesive material secures the flange to the skin surface. The adherence of the flange to the skin creates a limited, controlled pressure on the adhesive disc 20 which, in turn, presses the pressure plate 40 toward the skin surface. The pressure plate forces the nub onto the skin, exerting a mild pressure on the pressure point. The pressure plate allows the tension in the adhesive disc to translate onto the nub without the nub piercing the adhesive disc. The plate also permits the applicator to easily direct the nub to the pressure point. The firm connection between the nub and the plate allows the pressure to translate to the head of the nub. Since the nub is fixed to the adhesive disc by means of the pressure plate, the nub will not slip off the pressure point while it is being applied or when it is attached to the skin.

Referring to FIGS. 1 and 4, the flange 60 is sized in view of the size of the nub 10 such that a mild pressure is exerted. As the size of the flange and the nub are increased, the maximum applied pressure is also increased. The pressure should be strong enough to affect the flow of energy in the patient but not strong enough to cause discomfort or to pierce the skin. As currently preferred, the nub is about 2 mm high and has a diameter of about 4 mm. The pressure plate 40 has a diameter of about 8 mm. The adhesive ring 30 has an outer diameter of about 20 mm. Of course, these dimensions can be varied depending upon the patient and the pressure point.

The acupressure patch 100 may be applied by an acupressurist with instructions to the patient as to when to remove the patch. The patch could also be provided to the patient for application to the pressure point. The patient would need instruction regarding the proper location of the pressure, application of the acupressure patch, period of time in which the patch should be worn and any side effects of wearing the patch.

As discussed above, the nub 10 may be made of any substantially rigid material. In certain applications, however, it is desirable to provide a magnet 80 at the same point as the pressure. This may be particularly effective when the pressure and the magnet are applied at the same time. The nub may be made of a magnetized material, such as iron, thereby acting as a magnet. Alternatively, a magnet 80 may be inserted into the nub near the head 11 of the nub, such as in the cavity 15. Further, the nub may be made of a magnetizable material, such as iron, and an electric current passed through the material. Further, the pad 50 may be magnetic and inserted under the adhesive disc 20 such that, when the acupressure patch is applied to the skin, the magnet is proximate the skin surface.

While this invention has been described with reference to specific embodiments disclosed herein, it is not confined to the details set forth and the patent is intended to include modifications and changes which may come within and extend from the following claims.

I claim:

1. An apparatus for providing a controlled pressure to a selected point on the skin of a patient for a selected period of time comprising:

a flexible, adhesive disc having a first surface and a second surface, wherein adhesive is applied to the first surface;

a substantially flat, rigid pressure plate having a first face and a second face, wherein the second face is adhered to the first surface of the adhesive disc such that a portion of the adhesive disc extends beyond the plate, forming a flexible flange;

a rigid nub fixedly mounted to the pressure plate at a predetermined position on the first face of the pressure plate; and an adhesive ring having a first side, a second side and an aperture, wherein adhesive is disposed on the first side, the second side is in contact with the pressure plate and the adhesive disc, and the nub is disposed in the aperture.

2. The apparatus of claim 1 wherein the nub is integrally formed with the pressure plate.

3. The apparatus of claim 1 wherein the nub comprises a magnetizable material which is magnetized.

4. The apparatus of claim 1 further comprising a magnet mounted to the nub.

5. The apparatus of claim 1 further comprising a pad disposed between the adhesive disc and the pressure plate.

6. An acupressure patch for the application of a limited, controlled pressure to a precise point on the skin surface of a patient comprising:

a flexible adhesive disc having a first surface and a second surface which first surface has a disc surface area and wherein an adhesive material is applied to the first surface;

a rigid pressure plate having a substantially flat profile, a first face and a second face wherein the second face is adhered to the first surface of the adhesive disc and wherein the second face has a plate surface area which is less than the disc surface area such that a flexible flange is defined in the adhesive disc about the periphery of the pressure plate; and a rigid nub fixedly mounted to the first face of the plate, the nub having a head with a surface area which is less than the plate surface area.

7. The acupressure patch of claim 6 further comprising an adhesive ring having a first side, a second side and an aperture, wherein an adhesive material is applied to the first side of the adhesive ring, the second side of the adhesive ring contacts the first face of the pressure plate, the second side of the adhesive ring contacts the first surface of the adhesive disc, and the nub is disposed in the aperture.

8. The acupressure patch of claim 6 further comprising a magnet mounted to the adhesive disc.

9. The acupressure patch of claim 6 wherein the nub is a magnet.

10. The acupressure patch of claim 6 wherein the pressure plate is a magnet.

11. The acupressure patch of claim 6 further comprising a pad disposed between the adhesive disc and the pressure plate.

12. An acupressure patch for the application of a limited, controlled pressure to a precise point on the skin surface of a patient for an extended period of time comprising:

an adhesive disc having a first surface and a second surface wherein an adhesive material is applied to the first surface;

a rigid pressure plate having a substantially flat profile, a first face and a second face wherein the second face is adhered to the first surface of the adhesive disc such that a flange is defined in the adhesive disc about the periphery of the pressure plate;

a rigid nub fixedly mounted to the first face of the plate; and a magnet mounted to the adhesive disc at a fixed position.

13. The acupressure patch of claim 12 wherein the magnet is mounted in a cavity disposed in the nub.

14. The acupressure patch of claim 12 wherein the magnet is the nub.

15. The acupressure patch of claim 12 wherein the pressure plate and the nub are integrally formed of a magnetic material.

16. The acupressure patch of claim 12 further comprising a pad mounted to first surface of the adhesive disc between the adhesive disc and the pressure plate.

17. The acupressure patch of claim 12 further comprising an adhesive ring having a first side, a second side and an aperture, wherein adhesive is disposed on the first side, the second side is in contact with the pressure plate and the adhesive disc, and the nub is disposed in the aperture, the acupressure patch further comprising a removable release liner positioned contiguously over the first surface of the adhesive ring.

* * * * *